United States Patent [19]
Petersen et al.

[11] Patent Number: 5,635,518
[45] Date of Patent: Jun. 3, 1997

[54] N-SUBSTITUTED AZAHETEROCYCLIC CARBOXYLIC ACIDS AND ESTERS THEREOF

[75] Inventors: Hans Petersen, Vanløse; Knud E. Andersen, Smørum; Per O. Sørensen, Frederiksberg; Jesper Lau, Farum; Behrend F. Lundt, Kokkedal, all of Denmark

[73] Assignee: Novo Nordisk A/S, Bagsvaerd, Denmark

[21] Appl. No.: 263,634

[22] Filed: Jun. 22, 1994

[30] Foreign Application Priority Data

Jun. 23, 1993 [DK] Denmark .................. 0745/93

[51] Int. Cl.⁶ .................... A61K 31/445; C07D 211/60
[52] U.S. Cl. .................. 514/330; 514/319; 546/205; 546/227; 546/232; 546/236
[58] Field of Search .................. 546/205, 227, 546/232, 236; 514/330, 319

[56] References Cited

FOREIGN PATENT DOCUMENTS 0221572  11/1986  European Pat. Off. .
0252876   6/1987  European Pat. Off. .

OTHER PUBLICATIONS

Kikumoto, et al., J. Med. Chem., vol. 27 pp. 645–649, 1984.
CA 100:156,470X, 1984.
CA 108:186,587Y, 1988.
CA 113:97454P, 1990.

*Primary Examiner*—Ba K. Trinh
*Attorney, Agent, or Firm*—Steven T. Zelson, Esq.; Elias J. Lambiris, Esq.

[57] ABSTRACT

The present invention relates to therapeutically active azaheterocyclic compounds, a method of preparing the same and to pharmaceutical compositions comprising the compounds. The novel compounds are useful in treating a central nervous system ailment related to the GABA uptake.

13 Claims, No Drawings

N-SUBSTITUTED AZAHETEROCYCLIC CARBOXYLIC ACIDS AND ESTERS THEREOF

FIELD OF THE INVENTION

The present invention relates to novel N-substituted azaheterocyclic carboxylic acids and esters thereof in which a substituted alkyl chain forms part of the N-substituent and salts thereof, to methods for their preparation, to compositions containing them, and to their use for the clinical treatment of abnormal function of the γ-aminobutyric acid neurotransmission system.

BACKGROUND OF THE INVENTION

In recent years much pharmacological research concerning γ-aminobutyric acid (hereinafter designated GABA), an inhibitory neurotransmitter in the mammalian central nervous system, has been carried out.

The inhibition of GABA uptake results in enhanced availability of this inhibitory neurotransmitter in the synaptic cleft and thus to increased GABA'ergic activity. Increased GABA'ergic activity can be useful in the treatment, for example of anxiety, pain and epilepsy, as well as muscular and movement disorders (see, for example, P. Krogsgaard-Larsen et al., Progress in Medicinal Chemistry, 1985, 22, 68–112).

A well-known and potent inhibitor of GABA uptake from the synaptic cleft into presynaptic nerve terminals and glial cells is, for example, 3-piperidine-carboxylic acid (nipecotic acid). However, being a relatively compound and therefore unable to cross the blood-brain barrier, 3-piperidine-carboxylic acid itself has found no practical utility as a drug.

In U.S. Pat. No. 4,383,999 and 4,514,414 and in EP 236342 as well as in EP 231996 some derivatives of N-(4,4-disubstituted-3-butenyl)azahetero-cyclic carboxylic acids are claimed as inhibitors of GABA uptake. In EP 342635 and EP 374801, N-substituted azaheterocyclic carboxylic acids in which an oxime ether group and vinyl ether group forms part of the N-substituent respectively are claimed as inhibitors of GABA uptake. Further, in WO 9107389 and WO 9220658, N-substituted azacyclic carboxylic acids are claimed as inhibitors of GABA uptake. EP 221572 claims that 1-aryl-oxyalkylpyridine-3-carboxylic acids are inhibitors of GABA uptake.

According to Yunger, L. M. et al., J. Pharm. Exp. Ther. 1984, 228, 109, N-(4,4-diphenyl-3-buten-1-yl)nipecotic acid (designated SK&F 89976A), N-(4,4-diphenyl-3-buten-1-yl)guvacine (designated SK&F 100330A), N-(4,4-diphenyl-3-buten-1-yl)-homo-β-proline (designated SK&F 100561) and N-(4-phenyl-4-(2-thienyl)-3-buten-1-yl) nipecotic acid (designated SK&F 100604J) are orally active inhibitors of GABA uptake. These data are summarized in Krogsgaard-Larsen, P. et al., Epilepsy Res. 1987, 1, 77–93.

DESCRIPTION OF THE INVENTION

The present invention relates to novel N-substituted azaheterocyclic carboxylic acids and esters thereof of formula I

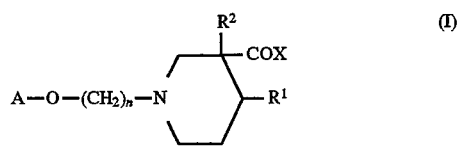

wherein

A is a saturated or unsaturated five or six-membered carbocyclic ring optionally substituted with a phenyl, benzylidene, $C_{1-4}$-alkyl substituted with phenyl or $C_{2-4}$-alkenyl substituted with phenyl which phenyl or benzylidene is optionally substituted with halogen, $C_{1-4}$-alkyl, $C_{1-4}$-alkoxy or trifluoromethyl and which saturated or unsaturated five or six-membered carbocyclic ring may be optionally fused with a benzo ring;

$R^1$ and $R^2$ represent hydrogen or may together represent a bond;

X is hydroxy or $C_{1-4}$-alkoxy;

n is 1, 2, 3, 4 or 5; or a pharmaceutically acceptable salt thereof.

The compounds of formula I may exist as geometric and optical isomers and all isomers and mixtures thereof are included herein. Isomers may be separated by means of standard methods such as chromatographic techniques or fractional crystallisation of suitable salts.

The compounds according to the invention may optionally exist as pharmaceutically acceptable acid addition salts or—when the carboxylic acid group is not esterified—as pharmaceutically acceptable metal salts or—optionally alkylated—ammonium salts.

Examples of such salts include inorganic and organic acid addition salts such as hydrochloride, hydrobromide, sulphate, phosphate, acetate, phthalate, fumarate, maleate, citrate, lactate, tartrate, oxalate, or similar pharmaceutically acceptable inorganic or organic acid addition salts, and include the pharmaceutically acceptable salts listed in Journal of Pharmaceutical Science, 66, 2 (1977) which are hereby incorporated by reference.

In a preferred embodiment of the invention $C_{1-4}$-alkyl is methyl or ethyl, $C_{1-4}$-alkenyl is ethylidene, $C_{1-4}$-alkoxy is methoxy or ethoxy, and X includes methoxy, ethoxy, isopropoxy or n-propoxy, and n includes 2, 3 or 4.

The compounds of formula I have a greater lipophilicity—and thus a greater availability to the brain—than the parent compounds without the N-substituent (i.e. nipecotic acid and guvacine).

It has been demonstrated that the novel compounds of formula I which inhibit the uptake of GABA from the synaptic cleft possess useful pharmacological properties in the central nervous system, in that they cause a selective enhancement of GABA'ergic activity. Compounds of formula I may be used to treat for example, pain, anxiety, extrapyrimidinal dyskinesia, epilepsy and certain muscular and movement disorders. They are also useful as sedatives, hypnotics and antidepressants.

The compounds of formula I are prepared by the following methods:

Method A:

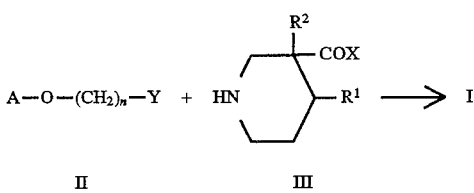

II   III

A compound of formula II wherein A and n are as defined above and Y is a suitable leaving group such as halogen, p-toluene sulphonate or mesylate may be reacted with an azaheterocyclic compound of formula III wherein $R^1$, $R^2$ and X are as defined above. This alkylation reaction may be carried out in a solvent such as acetone, dibutylether, 2-butanone, tetrahydrofuran, methylisobutylketone or toluene in the presence of a base e.g. potassium carbonate and a catalyst, e.g. an alkali metal iodide at a temperature up to reflux temperature for the solvent used for e.g. 1 to 120 h. If esters have been prepared in which X is alkoxy, compounds of formula I wherein X is OH may be prepared by hydrolysis of the ester group, preferably at room temperature in a mixture of an aqueous alkali metal hydroxide solution and an alcohol such as methanol or ethanol, for example, for about 0.5 to 6 h.

Method B:

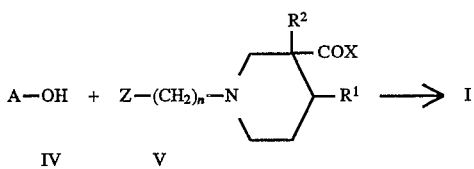

IV   V

A compound of formula IV wherein A is as defined above, may be reacted with a compound of formula V wherein $R^1$, $R^2$, n and X are as defined above and Z is a suitable leaving group such as halogen, p-toluene sulphonate or mesylate. This alkylation reaction may be carried out in a suitable solvent such as dibutylether, 2-butanone, tetrahydrofuran, methyl-isobutylketone or toluene in the presence of a base e.g. potassium carbonate or sodium hydride at a temperature up to reflux temperature for the solvent used for e.g. 1 to 120 h. If esters have been prepared in which X is alkoxy, compounds of formula I wherein X is OH may be prepared by hydrolysis of the ester group, preferably at room temperature in a mixture of an aqueous alkali metal hydroxide solution and an alcohol such as methanol or ethanol, for example, for about 0.5 to 6h.

Compounds of formula II, III and IV may readily be prepared by methods familiar to those skilled in the art. Compounds of formula V may be prepared according to the procedure described in U.S. Pat. No. 5,071,859.

Under certain circumstances it may be necessary to protect the intermediates used in the above methods e.g. a compound of formula III or V with suitable protecting groups. The carboxylic acid group can, for example, be esterified. Introduction and removal of such groups is described in "Protective Groups in Organic Synthesis" T. W. Greene and P. G. M. Wuts, 2ed. (John Wiley, 1991).

Pharmacological Methods

Values for in vitro inhibition of [$^3$H]-GABA uptake for the invention compounds were assessed essentially by the method of Fjalland (Acta Pharmacol. Toxicol. 1978, 42, 73–76).

Male wistar rat cortical tissue was gently homogenized by hand using a glass/PTFE homogenizer in 10 volumes of 0.32M sucrose. Incubation was performed in a 40 mM tris HCl buffer (pH 7.5 at 30° C.) containing 120 nM NaCl, 9.2 nM KCl, 4 mM $MgSO_4$, 2.3 nM $CaCl_2$ and 10 mM glucose, for 60 minutes at 30° C.

Values for inhibition of GABA uptake for some representative compounds are recorded in Table I.

TABLE I

| Inhibition of [$^3$H]-GABA uptake | |
|---|---|
| Example no. | $IC_{50}$ (μM) in vitro |
| 1 | 64 |
| 2 | 24 |
| 3 | 6.7 |
| 4 | 5.6 |
| 5 | 5.6 |

For the above indications the dosage will vary depending on the compound of formula I employed, on the mode of administration and on the therapy desired. However, in general, satisfactory results are obtained with a dosage of from about 0.5 mg to about 1000 mg, preferably from about 1 mg to about 500 mg of compounds of formula I, conveniently given from 1 to 5 times daily, optionally in sustained release form. Usually, dosage forms suitable for oral administration comprise from about 0.5 mg to about 1000 mg, preferably from about 1 mg to about 500 mg of the compounds of formula I admixed with a pharmaceutical carrier or diluent.

The compounds of formula I may be administered in pharmaceutically acceptable acid addition salt form or where possible as a metal or a lower alkylammonium salt.

This invention also relates to pharmaceutical compositions comprising a compound of formula I or a pharmaceutically acceptable salt thereof and, usually, such compositions also contains a pharmaceutical carrier or diluent. The compositions containing the compounds of this invention may be prepared by conventional techniques and appear in conventional forms, for example capsules, tablets, solutions or suspensions.

The pharmaceutical carrier employed may be a conventional solid or liquid carrier. Examples of solid carriers are lactose, terra alba, sucrose, talc, gelatin, agar, pectin, acacia, magnesium stearate and stearic acid. Examples of liquid carriers are syrup, peanut oil, olive oil and water.

Similarly, the carrier or diluent may include any time delay material known to the art, such as glyceryl monostearate or glyceryl distearate, alone or mixed with a wax.

If a solid carrier for oral administration is used, the preparation can be tabletted, placed in a hard gelatin capsule in powder or pellet form or it can be in the form of a troche or lozenge. The amount of solid carrier will vary widely, but will usually be from about 25 mg to about 1 g. If a liquid carrier is used, the preparation may be in the form of a syrup, emulsion, soft gelatin capsule or sterile injectable liquid such as an aqueous or non-aqueous liquid suspension or solution.

Generally, the compounds of this invention are dispended in unit dosage form comprising 50–200 mg of active ingredient in or together with a pharmaceutically acceptable carrier per unit dosage.

The dosage of the compounds according to this invention is 1–500 mg/day, e.g. about 100 mg per dose, when administered to patients, e.g. humans, as a drug.

A typical tablet, which may be prepared by conventional tabletting techniques contains:

| Core: | | |
|---|---|---|
| Active compound (as free compound or salt thereof) | | 100 mg |
| Colloidal silicon dioxide (Aerosil ®) | | 1.5 mg |
| Cellulose, microcryst. (Avicel ®) | | 70 mg |
| Modified cellulose gum (Ac-Di-Sol ®) | | 7.5 mg |
| Magnesium stearate | | |
| Coating: | | |
| HPMC | approx. | 9 mg |
| *Mywacett ® 9-40 T | approx. | 0.9 mg |

*Acylated monoglyceride used as plasticizer for film coating.

The route of administration may be any route, which effectively transports the active compound to the appropriate or desired site of action, such as oral or parenteral e.g. rectal, transdermal, subcutaneous, intravenous, intramuscular or intranasal, the oral route being preferred.

EXAMPLES

The process for preparing compounds of formula I is further illustrated in the following examples which however are not to be construed as limiting.

Hereinafter, TLC is thin layer chromatography and THF is tetrahydrofuran, $CDCl_3$ is deuterio chloroform and DMSO-$d_6$ is hexadeuterio dimethylsul-foxide. The structures of the compounds are confirmed by either elemental analysis or NMR, where peaks assigned to characteristic protons in the title compounds are presented where appropriate. NMR shifts ($\delta$) are given in parts per million (ppm). M.p. is melting point and is given in ° C. Column chromatography was carried out using the technique described by W. C. Still et al, J. Org. Chem. 1978, 43, 2923–2925 on Merck silica gel 60 (Art. 9385). Compounds used as starting materials are either known compounds or compounds which can readily be prepared by methods known per se.

Example 1

(R)-1-(2-Phenoxyethyl)-3-piperidinecarboxylic acid hydrochloride

A mixture of 2-phenoxyethylbromide (20 g, 100 mmol), (R)-3opiperidine-carboxylic acid ethyl ester (34 g, 112 mmol), potassium carbonate (41 g, 298 mmol) and methyl isobutylketone (200 ml) was heated at reflux overnight. The reaction mixture was allowed to cool and then filtered. The solvent was evaporated from the filtrate in vacuo and the residue was purified by column chromatography on silica gel (800 g, heptane/ethyl acetate =4/1) to give 17.1 g of (R)-1-(2-phenoxyethyl)-3-piperidine- carboxylic acid ethyl ester as an oil.

The above ester (3.5 g, 13 mmol) was dissolved in ethanol (35 ml) and 4N sodium hydroxide (3.2 ml) was added. The mixture was stirred at ambient temperature overnight. The reaction mixture was diluted with water and 4M hydrochloric acid (6.3 ml) was added. The mixture was concentrated in vacuo and dichloromethane (50 ml) and acetone were added to the residue. The mixture was concentrated in vacuo to give a solid residue which was heated at reflux with acetone (500 ml). The mixture was filtered while still hot and the filtrate was left overnight for crystallisation. The solid which formed was isolated by filtration and dried to give 1.0 g of the title compound as a solid.

M.p. 169°–170° C. Calculated for $C_{14}H_{19}NO_3 \cdot HCl$:
C, 58.8%; H, 7.1%; N, 4.9%; Found:
C, 58.8%; H, 7.2%; N, 4.8%.

Example 2

(R)-1-(4-Phenoxy-1-butyl)-3-piperidinecarboxylic acid hydrochloride

A mixture of 4-phenoxy-1-butylbromide (10 g, 44 mmol), (R)-3-piperidine-carboxylic acid ethyl ester (15 g, 44 mmol), potassium carbonate (18 g, 131 mmol) and methyl isobutylketone (100 ml) was heated at reflux overnight. The reaction mixture was allowed to cool and then filtered. The solvent was evaporated from the filtrate in vacuo and the residue was purified by column chromatography on silica gel (300 g, heptane/ethyl acetate=4/1) to give 12.1 g of (R)-1-(4-phenoxy-1-butyl)-3-piperidinecarboxylic acid ethyl ester as an oil.

The above ester (3.5 g, 11.5 mmol) was dissolved in ethanol (35 ml) and 4N sodium hydroxide (5.7 ml) was added. The mixture was stirred at ambient temperature overnight. The reaction mixture was diluted with water and 4M hydrochloric acid (11.5 ml) was added. The mixture was concentrated in vacuo and dichloromethane (50 ml) and acetone were added to the residue. The mixture was concentrated in vacuo to give a residue which was heated at reflux with acetone (700 ml). The mixture was filtered while still hot and the filtrate was left for crystallisation. The solid which formed was isolated by filtration and dried to give 1.9 g of the title compound as a solid.

M.p. 176°–177° C. Calculated for $C_{16}H_{23}NO_3 \cdot HCl$:
C, 61.2%; H, 7.7%; N, 4.5%; Found:
C, 61.4%; H, 7.9%; N, 4.5%.

Example 3

(R)-1-(2-(2-Benzylphenoxy)ethyl)-3-piperidinecarboxylic acid hydrochloride

Sodium hydride (0.8 g, 20 mmol, 60% oil dispersion) was added portionwise to a stirred solution of 2-benzylphenol (1.8 g, 10 mmol) in toluene (30 ml) placed under an atmosphere of nitrogen. The mixture was stirred for 30 minutes and (R)-1-(2-bromoethyl)-3-piperidinecarboxylic acid ethyl ester hydrobromide (3.5 g, 10 mmol, EP 374801) was added portionwise. The reaction mixture was stirred for 2 h at ambient temperature and water (50 ml) was added. The phases were separated and the organic phase was extracted with a 10% citric acid solution (200 ml). This acidic solution was extracted with a small portion of toluene and the organic extracts were discarded. To the acidic aqueous phase 4N sodium hydroxide was added until pH 7–8 and the mixture was extracted with ethyl acetate (150 ml). The organic extract was dried ($Na_2SO_4$) and the solvent was evaporated in vacuo to give 1.7 g of (R)-1-(2-(2-benzylphenoxy)ethyl)-3-piperidine-carboxylic acid ethyl ester as an oil.

The above ester (1.7 g, 4.6 mmol) was dissolved in ethanol (10 ml) and 4N sodium hydroxide (3.5 ml) was added. The mixture was stirred at ambient temperature for 5 h. Excess concentrated hydrochloric acid was added followed by dichloromethane (300 ml). The phases were separated and the organic phase was dried ($Na_2SO_4$). The solvent was evaporated in vacuo to give a foamy residue which was dissolved in acetone (15 ml). The solid which formed was isolated by filtration and dried to give 1.3 g of the title compound as a solid.

M.p. 165°–167° C. Calculated for $C_{21}H_{25}NO_3 \cdot HCl$:
C, 67.1%; H, 7.0%; N, 3.7%; Found:
C, 66.9%; H, 7.0%; N, 3.4%.

Example 4

(R)-1-(2-(3-Phenylphenoxy)ethyl)-3-piperidinecarboxylic acid hydrochloride

Sodium hydride (0.46 g, 11.6 mmol, 60% oil dispersion) was added portionwise to a stirred solution of 3-hydroxybiphenyl (0.99 g, 5.8 mmol) in toluene (30 ml) placed under an atmosphere of nitrogen. The mixture was stirred for 30 minutes and (R)-1-(2-bromoethyl)-3-piperidinecarboxylic acid ethyl ester hydrobromide (2.0 g, 5.8 mmol, EP 374801) was added portionwise. The reaction mixture was stirred overnight at ambient temperature and water was added (50 ml). The phases were separated and the aqueous phase was extracted with toluene (20 ml). The solvent was evaporated in vacuo from the combined organic phases to give a residue which was dissolved in ethyl acetate (100 ml). Water (50 ml) was added and pH was adjusted to 4 with a 34% tartaric acid solution. The phases were separated and the organic phase extracted with 34% tartaric acid (2×5 ml). To the combined aqueous phases was added ethyl acetate (30 ml) and pH was adjusted to 7.5 with 2N sodium hydroxide. The organic phase was washed with brine (10 ml) and dried ($Na_2SO_4$). The solvent was evaporated in vacuo to give 1.5 g of (R)-1-(2-(3-Phenylphenoxy)ethyl)-3-piperidinecarboxylic acid ethyl ester as an oil.

The above ester (1.4 g, 4 mmol) was dissolved in ethanol (30 ml) and 4N sodium hydroxide (4.5 ml) was added. The mixture was stirred at ambient temperature overnight. The reaction mixture was concentrated in vacuo to give a residue to which dichloromethane (175 ml) was added. The mixture was placed on an icebath and concentrated hydrochloric acid (2.1 ml) was added. The phases were separated and the organic phase was dried ($Na_2SO_4$). The solvent was evaporated in vacuo to give a residue which was dissolved in a mixture of dichloromethane (175 ml) and a small portion of water. The phases were separated and the organic phase was dried ($Na_2SO_4$). The solvent was evaporated in vacuo to give 0.4 g of the title compound as an oil.

$^1$H NMR (DMSO-$d_6$) δ 4.55 (brs, 2H).

Example 5

(R)-1-(2-(2-Phenylphenoxy)ethyl)-3-piperidinecarboxylic acid hydrochloride

A mixture of 2-hydroxybiphenyl (3.0 g, 17.6 mmol), (R)-1-(2-bromoethyl)-3-piperidinecarboxylic acid ethyl ester hydrobromide (6.1 g, 17.6 mmol, EP 374801), potassium carbonate (9.7 g, 71 mmol) and methyl isobutylketone (50 ml) was heated at reflux for 22 h. The reaction mixture was allowed to cool, diluted with methyl isobutylketone and filtered. The solvent was evaporated in vacuo and the residue was purified by column chromatography (heptane/ethyl acetate=2/3) to give 2.7 g of (R)-1-(2-(2-phenylphenoxy)ethyl)-3-piperidinecarboxylic acid ethyl ester as an oil.

The above ester (2.0 g, 5.7 mmol) was dissolved in ethanol (25 ml) and 4N sodium hydroxide (6.4 ml) was added. The mixture was stirred at ambient temperature for 3 h. Excess concentrated hydrochloric acid was added followed by a small portion of water. The mixture was concentrated in vacuo and dichloromethane (100 ml) and water (25 ml) were added. The phases were separated and the organic phase was dried ($Na_2S_4$). The solvent was evaporated in vacuo to give a solid residue which was recrystallised from acetone to give 1.2 g of title compound as a solid. M.p. 171°–172° C. Calculated for $C_{20}H_{23}NO_3 \cdot HCl$: C, 66.4%; H, 6.7%; N, 3.9%; Found: C, 66.4%; H, 6.8%; N, 3.7%.

We claim:

1. A compound of formula I

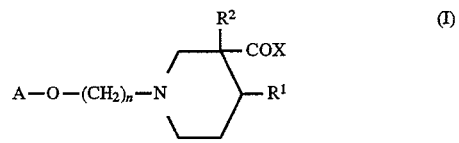

wherein

A is a saturated or unsaturated five or six-membered carbocyclic ring substituted with (a) phenyl or benzylidene, each of which is optionally substituted with halogen, $C_{1-4}$-alkyl, $C_{1-4}$-alkoxy or trifluoromethyl; (b) $C_{1-4}$-alkyl substituted with phenyl or (c) $C_{1-4}$-alkenyl substituted with phenyl; wherein the saturated or unsaturated five or six-membered carbocyclic ring is optionally fused with a benzo ring;

$R^1$ and $R^2$ are hydrogen or form a bond;

X is hydroxy or $C_{1-4}$-alkoxy;

n is 1, 2, 3, 4 or 5; or a pharmaceutically acceptable salt thereof.

2. The compound according to claim 1, wherein $R^1$ and $R^2$ form a bond.

3. The compound according to claim 1, wherein the saturated or unsaturated five or six-membered carbocyclic ring is fused with a benzo ring.

4. The compound according to claim 1, wherein A is a phenyl ring which is optionally substituted.

5. The compound according to claim 4, wherein the phenyl ring is fused with a benzo ring.

6. The compound according to claim 4, wherein $R^1$ and $R^2$ form a bond.

7. The compound according to claim 1 which is (R)-1-(2-(2-Benzylphenoxy)ethyl)-3-piperidinecarboxylic acid or a pharmaceutically acceptable salt thereof.

8. The compound according to claim 1 which is (R)-1-(2-(3-Phenylphenoxy)ethyl)-3-piperidinecarboxylic acid or a pharmaceutically acceptable salt thereof.

9. The compound according to claim 1 which is (R)-1-(2-(2-Phenylphenoxy)ethyl)-3-piperidinecarboxylic acid or a pharmaceutically acceptable salt thereof.

10. A pharmaceutical composition comprising a compound according to claim 1 together with a pharmaceutically acceptable carrier or diluent.

11. The pharmaceutical composition according to claim 10, wherein the compound is present in an amount between 0.5 mg and 1000 mg per unit dose.

12. A method of treating a central nervous system ailment related to GABA uptake in a subject in need of such treatment comprising administering to said subject an effective amount of a compound according to claim 1.

13. A method of treating a central nervous system ailment related to GABA uptake in a subject in need of such treatment comprising administering to said subject a pharmaceutical composition according to claim 10.

* * * * *